(12) United States Patent
Sheng et al.

(10) Patent No.: US 11,932,881 B2
(45) Date of Patent: Mar. 19, 2024

(54) HEPARIN SKELETON SYNTHASE AND ITS MUTANTS AND APPLICATION

(71) Applicants: SHAN DONG UNIVERSITY, Jinan (CN); Bloomage Biotechnology Corporation Limited, Jinan (CN)

(72) Inventors: Juzheng Sheng, Jinan (CN); Xueping Guo, Jinan (CN); Jianqun Deng, Jinan (CN); Fengshan Wang, Jinan (CN); Zhen Lu, Jinan (CN); Ranran Du, Jinan (CN); Liu Sun, Jinan (CN); Yuanjun Sun, Jinan (CN)

(73) Assignees: SHAN DONG UNIVERSITY, Jinan (CN); Bloomage Biotechnology Corporation Limited, Jinan (CN)

( * ) Notice: Subject to any disclaimer, the term of this patent is extended or adjusted under 35 U.S.C. 154(b) by 0 days.

(21) Appl. No.: 17/646,773

(22) Filed: Jan. 3, 2022

(65) Prior Publication Data
US 2022/0267746 A1 Aug. 25, 2022

(30) Foreign Application Priority Data
Feb. 20, 2021 (CN) .......................... 202110192424.2

(51) Int. Cl.
C12N 9/00 (2006.01)
C12N 9/10 (2006.01)
C12N 15/10 (2006.01)
C12N 15/70 (2006.01)
C12P 19/64 (2006.01)

(52) U.S. Cl.
CPC .......... *C12N 9/1051* (2013.01); *C12N 15/102* (2013.01); *C12N 15/70* (2013.01); *C12P 19/64* (2013.01); *C12N 2800/101* (2013.01)

(58) Field of Classification Search
CPC ..... C12N 9/1048; C12N 9/1051; C12P 19/04; C12P 19/26; A61K 47/36; C08B 37/006
USPC .......................... 435/71, 320, 1, 252.3, 101
See application file for complete search history.

(56) References Cited

PUBLICATIONS

Vecca et al. PLOS one, Oct. 25, 2016, pp. 1-17.*

* cited by examiner

*Primary Examiner* — Robert B Mondesi
*Assistant Examiner* — Mohammad Y Meah
(74) *Attorney, Agent, or Firm* — CBM PATENT CONSULTING, LLC

(57) ABSTRACT

A heparin skeleton synthase originates from *Neisseria animaloris*, with an amino acid sequence as shown in SEQ ID NO.2 and a nucleotide sequence of the coding gene as shown in SEQ ID NO.1. Its recombinant expression level is 6.8 times that of the existing heparin skeleton synthase KfiA from *Escherichia coli* K5, and total enzyme activity per fermentation liquor is 5.22 times that of the heparin skeleton synthase KfiA. The heparin skeleton synthase mutants obtained through site-directed mutagenesis of the sites No. 16, No. 25, No. 30, No. 111, No. 165, and No. 172 in the amino acid sequence of the said heparin skeleton synthase all have high expression levels.

7 Claims, 9 Drawing Sheets

Specification includes a Sequence Listing.

SEQUENCE LISTING

<160> NUMBER OF SEQ ID NOS: 14

<210> SEQ ID NO 1
<211> LENGTH: 735
<212> TYPE: DNA
<213> ORGANISM: Neisseria animalis

<400> SEQUENCE: 1

```
atgataatag ctaatatggc aacatttccc gctagggtag aaatatgtaa acaagtggtt    60
gatagcatct acaaccaggt tgaccaaatt aacctgtgct tcaacgagtt taagcagatc   120
ccgaaagaat acgcgaagta tcacaaactg aacccggtga ttccggatac cgactataag   180
gatgttggta aatttgtgca caaagttagc gataacgacg aggtgatcct gattgacgat   240
gacatcattt acccgcgtga ctatgtggaa gttctgcgtt acttctataa gaaataccaa   300
cacctgaaca tcattgttgg tacccacggc atcatttacc cggatctgta tgacggcagc   360
gtgagcagcc gtaaggtttt caccttaaa cacagcctga agcgtccgcg tgtggttaac   420
cagctgggta ccggcaccgt gtacctgaaa ggtagccaaa tgccgagcct ggagtatatg   480
aagggcagcc agagcttcgt ggatgttcgt tttagcaaat acatgttcga aagggtatc   540 ggcctgatct gcattccgcg tggtgcggat tggcaaaagg agatcaaaca ggaagacagc   600
```

```
atttcaaca actttaccag caaatggccg atgcaggtga tccaagaagt tcagatcatt    660
gcgggctata gcaagctgcc gtttaacctg gttaaagaga ttgaattcaa caaggacagc    720
ctgctgatga gccaa                                                    735
```

<210> SEQ ID NO 2
<211> LENGTH: 245
<212> TYPE: PRT
<213> ORGANISM: Neisseria animalis

<400> SEQUENCE: 2

```
Met Ile Ile Ala Asn Met Ala Thr Phe Pro Ala Arg Val Glu Ile Cys
1               5                   10                  15

Lys Gln Val Val Asp Ser Ile Tyr Asn Gln Val Asp Gln Ile Asn Leu
            20                  25                  30

Cys Phe Asn Glu Phe Lys Gln Ile Pro Lys Glu Tyr Ala Lys Tyr His
        35                  40                  45

Lys Leu Asn Pro Val Ile Pro Asp Thr Asp Tyr Lys Asp Val Gly Lys
    50                  55                  60

Phe Val His Lys Val Ser Asp Asn Asp Glu Val Ile Leu Ile Asp Asp
65                  70                  75                  80

Asp Ile Ile Tyr Pro Arg Asp Tyr Val Glu Val Leu Arg Tyr Phe Tyr
                85                  90                  95

Lys Lys Tyr Gln His Leu Asn Ile Ile Val Gly Thr His Gly Ile Ile
            100                 105                 110

Tyr Pro Asp Leu Tyr Asp Gly Ser Val Ser Ser Arg Lys Val Phe Thr
        115                 120                 125

Phe Lys His Ser Leu Lys Arg Pro Arg Val Val Asn Gln Leu Gly Thr
    130                 135                 140

Gly Thr Val Tyr Leu Lys Gly Ser Gln Met Pro Ser Leu Glu Tyr Met
145                 150                 155                 160

Lys Gly Ser Gln Ser Phe Val Asp Val Arg Phe Ser Lys Tyr Met Phe
                165                 170                 175

Glu Lys Gly Ile Gly Leu Ile Cys Ile Pro Arg Gly Ala Asp Trp Gln
            180                 185                 190

Lys Glu Ile Lys Gln Glu Asp Ser Ile Phe Asn Asn Phe Thr Ser Lys
        195                 200                 205

Trp Pro Met Gln Val Ile Gln Glu Val Gln Ile Ile Ala Gly Tyr Ser
    210                 215                 220

Lys Leu Pro Phe Asn Leu Val Lys Glu Ile Glu Phe Asn Lys Asp Ser
225                 230                 235                 240

Leu Leu Met Ser Gln
            245
```

<210> SEQ ID NO 3
<211> LENGTH: 735
<212> TYPE: DNA
<213> ORGANISM: Artificial Sequence
<220> FEATURE:
<223> OTHER INFORMATION: It is synthesized.

<400> SEQUENCE: 3

```
atgataatag ctaatatggc aacatttccc gctagggtag aaatactgaa acaagtggtt    60
gatagcatct acaaccaggt tgaccaaatt aacctgtgct caacgagtt taagcagatc    120 ccgaaagaat acgcgaagta tcacaaactg aacccggtga ttccggatac cgactataag    180
```

```
gatgttggta aatttgtgca caaagttagc gataacgacg aggtgatcct gattgacgat    240
gacatcattt acccgcgtga ctatgtggaa gttctgcgtt acttctataa gaaataccaa    300
cacctgaaca tcattgttgg tacccacggc atcatttacc cggatctgta tgacggcagc    360
gtgagcagcc gtaaggtttt cacctttaaa cacagcctga agcgtccgcg tgtggttaac    420
cagctgggta ccggcaccgt gtacctgaaa ggtagccaaa tgccgagcct ggagtatatg    480
aagggcagcc agagcttcgt ggatgttcgt tttagcaaat acatgttcga aaagggtatc    540
ggcctgatct gcattccgcg tggtgcggat tggcaaaagg agatcaaaca ggaagacagc    600
attttcaaca actttaccag caaatggccg atgcaggtga tccaagaagt tcagatcatt    660
gcgggctata gcaagctgcc gtttaacctg gttaaagaga ttgaattcaa caaggacagc    720
ctgctgatga gccaa                                                    735
```

```
<210> SEQ ID NO 4
<211> LENGTH: 245
<212> TYPE: PRT
<213> ORGANISM: Artificial Sequence
<220> FEATURE:
<223> OTHER INFORMATION: It is synthesized.

<400> SEQUENCE: 4

Met Ile Ile Ala Asn Met Ala Thr Phe Pro Ala Arg Val Glu Ile Leu
1               5                   10                  15

Lys Gln Val Val Asp Ser Ile Tyr Asn Gln Val Asp Gln Ile Asn Leu
            20                  25                  30

Cys Phe Asn Glu Phe Lys Gln Ile Pro Lys Glu Tyr Ala Lys Tyr His
        35                  40                  45

Lys Leu Asn Pro Val Ile Pro Asp Thr Asp Tyr Lys Asp Val Gly Lys
    50                  55                  60

Phe Val His Lys Val Ser Asp Asn Asp Glu Val Ile Leu Ile Asp Asp
65                  70                  75                  80

Asp Ile Ile Tyr Pro Arg Asp Tyr Val Glu Val Leu Arg Tyr Phe Tyr
                85                  90                  95

Lys Lys Tyr Gln His Leu Asn Ile Ile Val Gly Thr His Gly Ile Ile
            100                 105                 110

Tyr Pro Asp Leu Tyr Asp Gly Ser Val Ser Ser Arg Lys Val Phe Thr
        115                 120                 125

Phe Lys His Ser Leu Lys Arg Pro Arg Val Val Asn Gln Leu Gly Thr
    130                 135                 140

Gly Thr Val Tyr Leu Lys Gly Ser Gln Met Pro Ser Leu Glu Tyr Met
145                 150                 155                 160

Lys Gly Ser Gln Ser Phe Val Asp Val Arg Phe Ser Lys Tyr Met Phe
                165                 170                 175

Glu Lys Gly Ile Gly Leu Ile Cys Ile Pro Arg Gly Ala Asp Trp Gln
            180                 185                 190

Lys Glu Ile Lys Gln Glu Asp Ser Ile Phe Asn Asn Phe Thr Ser Lys
        195                 200                 205

Trp Pro Met Gln Val Ile Gln Glu Val Gln Ile Ile Ala Gly Tyr Ser
    210                 215                 220

Lys Leu Pro Phe Asn Leu Val Lys Glu Ile Glu Phe Asn Lys Asp Ser
225                 230                 235                 240

Leu Leu Met Ser Gln
                245
```

<210> SEQ ID NO 5
<211> LENGTH: 735
<212> TYPE: DNA
<213> ORGANISM: Artificial Sequence
<220> FEATURE:
<223> OTHER INFORMATION: It is synthesized.

<400> SEQUENCE: 5

```
atgataatag ctaatatggc aacatttccc gctagggtag aaatatgtaa acaagtggtt    60
gatagcatct acccgcaggt tgaccaaatt aacctgtgct tcaacgagtt taagcagatc   120
ccgaaagaat acgcgaagta tcacaaactg aacccggtga ttccggatac cgactataag   180
gatgttggta aatttgtgca caaagttagc gataacgacg aggtgatcct gattgacgat   240
gacatcattt acccgcgtga ctatgtggaa gttctgcgtt acttctataa gaaataccaa   300
cacctgaaca tcattgttgg tacccacggc atcatttacc cggatctgta tgacggcagc   360
gtgagcagcc gtaaggtttt cacctttaaa cacagcctga gcgtccgcg tgtggttaac    420
cagctgggta ccggcaccgt gtacctgaaa ggtagccaaa tgccgagcct ggagtatatg   480
aagggcagcc agagcttcgt ggatgttcgt tttagcaaat acatgttcga aagggtatc    540
ggcctgatct gcattccgcg tggtgcggat tggcaaaagg agatcaaaca ggaagacagc   600
attttcaaca actttaccag caaatggccg atgcaggtga tccaagaagt tcagatcatt   660
gcgggctata gcaagctgcc gtttaacctg gttaaagaga ttgaattcaa caaggacagc   720
ctgctgatga gccaa                                                    735
```

<210> SEQ ID NO 6
<211> LENGTH: 245
<212> TYPE: PRT
<213> ORGANISM: Artificial Sequence
<220> FEATURE:
<223> OTHER INFORMATION: It is synthesized.

<400> SEQUENCE: 6

Met Ile Ile Ala Asn Met Ala Thr Phe Pro Ala Arg Val Glu Ile Cys
1               5                   10                  15

Lys Gln Val Val Asp Ser Ile Tyr Pro Gln Val Asp Gln Ile Asn Leu
            20                  25                  30

Cys Phe Asn Glu Phe Lys Gln Ile Pro Lys Glu Tyr Ala Lys Tyr His
        35                  40                  45

Lys Leu Asn Pro Val Ile Pro Asp Thr Asp Tyr Lys Asp Val Gly Lys
    50                  55                  60

Phe Val His Lys Val Ser Asp Asn Asp Glu Val Ile Leu Ile Asp Asp
65                  70                  75                  80

Asp Ile Ile Tyr Pro Arg Asp Tyr Val Glu Val Leu Arg Tyr Phe Tyr
                85                  90                  95

Lys Lys Tyr Gln His Leu Asn Ile Ile Val Gly Thr His Gly Ile Ile
            100                 105                 110

Tyr Pro Asp Leu Tyr Asp Gly Ser Val Ser Ser Arg Lys Val Phe Thr
        115                 120                 125

Phe Lys His Ser Leu Lys Arg Pro Arg Val Val Asn Gln Leu Gly Thr
    130                 135                 140

Gly Thr Val Tyr Leu Lys Gly Ser Gln Met Pro Ser Leu Glu Tyr Met
145                 150                 155                 160

Lys Gly Ser Gln Ser Phe Val Asp Val Arg Phe Ser Lys Tyr Met Phe
                165                 170                 175

Glu Lys Gly Ile Gly Leu Ile Cys Ile Pro Arg Gly Ala Asp Trp Gln 180                 185                 190
Lys Glu Ile Lys Gln Glu Asp Ser Ile Phe Asn Asn Phe Thr Ser Lys
                195                 200                 205

Trp Pro Met Gln Val Ile Gln Glu Val Gln Ile Ile Ala Gly Tyr Ser
    210                 215                 220

Lys Leu Pro Phe Asn Leu Val Lys Glu Ile Glu Phe Asn Lys Asp Ser
225                 230                 235                 240

Leu Leu Met Ser Gln
            245

<210> SEQ ID NO 7
<211> LENGTH: 735
<212> TYPE: DNA
<213> ORGANISM: Artificial Sequence
<220> FEATURE:
<223> OTHER INFORMATION: It is synthesized.

<400> SEQUENCE: 7

```
atgataatag ctaatatggc aacatttccc gctagggtag aaatatgtaa acaagtggtt      60
gatagcatct acaaccaggt tgaccaactg aacctgtgct tcaacgagtt taagcagatc     120
ccgaaagaat acgcgaagta tcacaaactg aacccgtgta ttccggatac cgactataag     180
gatgttggta aatttgtgca caagttagc gataacgacg aggtgatcct gattgacgat     240
gacatcattt acccgcgtga ctatgtggaa gttctgcgtt acttctataa gaatacccaa     300
cacctgaaca tcattgttgg tacccacggc atcatttacc cggatctgta tgacggcagc     360
gtgagcagcc gtaaggtttt cacctttaaa cacagcctga gcgtccgcg tgtggttaac     420
cagctgggta ccggcaccgt gtacctgaaa ggtagccaaa tgccgagcct ggagtatatg     480
aagggcagcc agagcttcgt ggatgttcgt tttagcaaat acatgttcga aaagggtatc     540
ggcctgatct gcattccgcg tggtgcggat tggcaaaagg agatcaaaca ggaagacagc     600
attttcaaca actttaccag caaatggccg atgcaggtgt ccaagaagt tcagatcatt     660
gcgggctata gcaagctgcc gtttaacctg gttaagagaa ttgaattcaa caaggacagc     720
ctgctgatga gccaa                                                      735
```

<210> SEQ ID NO 8
<211> LENGTH: 245
<212> TYPE: PRT
<213> ORGANISM: Artificial Sequence
<220> FEATURE:
<223> OTHER INFORMATION: It is synthesized.

<400> SEQUENCE: 8

Met Ile Ile Ala Asn Met Ala Thr Phe Pro Ala Arg Val Glu Ile Cys
1               5                   10                  15

Lys Gln Val Val Asp Ser Ile Tyr Asn Gln Val Asp Gln Leu Asn Leu
            20                  25                  30

Cys Phe Asn Glu Phe Lys Gln Ile Pro Lys Glu Tyr Ala Lys Tyr His
        35                  40                  45

Lys Leu Asn Pro Val Ile Pro Asp Thr Asp Tyr Lys Asp Val Gly Lys
    50                  55                  60

Phe Val His Lys Val Ser Asp Asn Asp Glu Val Ile Leu Ile Asp Asp
65                  70                  75                  80

Asp Ile Ile Tyr Pro Arg Asp Tyr Val Glu Val Leu Arg Tyr Phe Tyr
                85                  90                  95

Lys Lys Tyr Gln His Leu Asn Ile Ile Val Gly Thr His Gly Ile Ile

Tyr Pro Asp Leu Tyr Asp Gly Ser Val Ser Arg Lys Val Phe Thr
            100                 105                 110
Phe Lys His Ser Leu Lys Arg Pro Arg Val Val Asn Gln Leu Gly Thr
            115                 120                 125
Gly Thr Val Tyr Leu Lys Gly Ser Gln Met Pro Ser Leu Glu Tyr Met
145             130            150            155            160
Lys Gly Ser Gln Ser Phe Val Asp Val Arg Phe Ser Lys Tyr Met Phe
                165                 170                 175
Glu Lys Gly Ile Gly Leu Ile Cys Ile Pro Arg Gly Ala Asp Trp Gln
                180                 185                 190
Lys Glu Ile Lys Gln Glu Asp Ser Ile Phe Asn Asn Phe Thr Ser Lys
                195                 200                 205
Trp Pro Met Gln Val Ile Gln Glu Val Gln Ile Ile Ala Gly Tyr Ser
            210                 215                 220
Lys Leu Pro Phe Asn Leu Val Lys Glu Ile Glu Phe Asn Lys Asp Ser
225             230                 235                 240
Leu Leu Met Ser Gln
            245

<210> SEQ ID NO 9
<211> LENGTH: 735
<212> TYPE: DNA
<213> ORGANISM: Artificial Sequence
<220> FEATURE:
<223> OTHER INFORMATION: It is synthesized.

<400> SEQUENCE: 9

| | | | | | |
|---|---|---|---|---|---|
| atgataatag | ctaatatggc | aacatttccc | gctagggtag | aaatatgtaa | acaagtggtt | 60 |
| gatagcatct | acaaccaggt | tgaccaaatt | aacctgtgct | tcaacgagtt | taagcagatc | 120 |
| ccgaaagaat | acgcgaagta | tcacaaactg | aacccggtga | ttccggatac | cgactataag | 180 |
| gatgttggta | aatttgtgca | caaagttagc | gataacgacg | aggtgatcct | gattgacgat | 240 |
| gacatcattt | acccgcgtga | ctatgtggaa | gttctgcgtt | acttctataa | gaaataccaa | 300 |
| cacctgaaca | tcattgttgg | tacccacggc | tccatttacc | cggatctgta | tgacggcagc | 360 |
| gtgagcagcc | gtaaggtttt | cacctttaaa | cacagcctga | agcgtccgcg | tgtggttaac | 420 |
| cagctgggta | ccggcaccgt | gtacctgaaa | ggtagccaaa | tgccgagcct | ggagtatatg | 480 |
| aagggcagcc | agagcttcgt | ggatgttcgt | tttagcaaat | acatgttcga | aagggtatc | 540 |
| ggcctgatct | gcattccgcg | tggtgcggat | tggcaaaagg | agatcaaaca | ggaagacagc | 600 |
| attttcaaca | actttaccag | caaatggccg | atgcaggtga | tccaagaagt | tcagatcatt | 660 |
| gcgggctata | gcaagctgcc | gtttaacctg | gttaaagaga | ttgaattcaa | caaggacagc | 720 |
| ctgctgatga | gccaa | | | | | 735 |

<210> SEQ ID NO 10
<211> LENGTH: 245
<212> TYPE: PRT
<213> ORGANISM: Artificial Sequence
<220> FEATURE:
<223> OTHER INFORMATION: It is synthesized.

<400> SEQUENCE: 10

Met Ile Ile Ala Asn Met Ala Thr Phe Pro Ala Arg Val Glu Ile Cys
1               5                   10                  15
Lys Gln Val Val Asp Ser Ile Tyr Asn Gln Val Asp Gln Ile Asn Leu

```
              20                  25                  30
Cys Phe Asn Glu Phe Lys Gln Ile Pro Lys Glu Tyr Ala Lys Tyr His
             35                  40                  45

Lys Leu Asn Pro Val Ile Pro Asp Thr Asp Tyr Lys Asp Val Gly Lys
 50                  55                  60

Phe Val His Lys Val Ser Asp Asn Asp Glu Val Ile Leu Ile Asp Asp
 65                  70                  75                  80

Asp Ile Ile Tyr Pro Arg Asp Tyr Val Glu Val Leu Arg Tyr Phe Tyr
                 85                  90                  95

Lys Lys Tyr Gln His Leu Asn Ile Ile Val Gly Thr His Gly Ser Ile
                100                 105                 110

Tyr Pro Asp Leu Tyr Asp Gly Ser Val Ser Ser Arg Lys Val Phe Thr
            115                 120                 125

Phe Lys His Ser Leu Lys Arg Pro Arg Val Val Asn Gln Leu Gly Thr
        130                 135                 140

Gly Thr Val Tyr Leu Lys Gly Ser Gln Met Pro Ser Leu Glu Tyr Met
145                 150                 155                 160

Lys Gly Ser Gln Ser Phe Val Asp Val Arg Phe Ser Lys Tyr Met Phe
                165                 170                 175

Glu Lys Gly Ile Gly Leu Ile Cys Ile Pro Arg Gly Ala Asp Trp Gln
                180                 185                 190

Lys Glu Ile Lys Gln Glu Asp Ser Ile Phe Asn Asn Phe Thr Ser Lys
            195                 200                 205

Trp Pro Met Gln Val Ile Gln Glu Val Gln Ile Ile Ala Gly Tyr Ser
        210                 215                 220

Lys Leu Pro Phe Asn Leu Val Lys Glu Ile Glu Phe Asn Lys Asp Ser
225                 230                 235                 240

Leu Leu Met Ser Gln
            245

<210> SEQ ID NO 11
<211> LENGTH: 735
<212> TYPE: DNA
<213> ORGANISM: Artificial Sequence
<220> FEATURE:
<223> OTHER INFORMATION: It is synthesized.

<400> SEQUENCE: 11
atgataatag ctaatatggc aacatttccc gctagggtag aaatatgtaa acaagtggtt    60
gatagcatct acaaccaggt tgaccaaatt aacctgtgct caacgagtt taagcagatc    120 ccgaaagaat acgcgaagta tcacaaactg aacccggtga ttccggatac cgactataag    180
gatgttggta aatttgtgca caaagttagc gataacgacg aggtgatcct gattgacgat    240
gacatcattt acccgcgtga ctatgtggaa gttctgcgtt acttctataa gaaataccaa    300
cacctgaaca tcattgttgg tacccacggc atcatttacc cggatctgta tgacggcagc    360
gtgagcagcc gtaaggtttt cacctttaaa cacagcctga gcgtccgcg tgtggttaac    420 cagctgggta ccggcaccgt gtacctgaaa ggtagccaaa tgccgagcct ggagtatatg    480
aagggcagcc agaaattcgt ggatgttcgt tttagcaaat acatgttcga aagggtatc    540 ggcctgatct gcattccgcg tggtgcggat tggcaaaagg agatcaaaca ggaagacagc    600
attttcaaca actttaccag caaatggccg atgcaggtga tccaagaagt tcagatcatt    660
gcgggctata gcaagctgcc gtttaacctg gttaagaga ttgaattcaa caaggacagc    720
ctgctgatga gccaa                                                    735
```

<210> SEQ ID NO 12
<211> LENGTH: 245
<212> TYPE: PRT
<213> ORGANISM: Artificial Sequence
<220> FEATURE:
<223> OTHER INFORMATION: It is synthesized.

<400> SEQUENCE: 12

```
Met Ile Ile Ala Asn Met Ala Thr Phe Pro Ala Arg Val Glu Ile Cys
1               5                  10                  15

Lys Gln Val Val Asp Ser Ile Tyr Asn Gln Val Asp Gln Ile Asn Leu
            20                  25                  30

Cys Phe Asn Glu Phe Lys Gln Ile Pro Lys Glu Tyr Ala Lys Tyr His
        35                  40                  45

Lys Leu Asn Pro Val Ile Pro Asp Thr Asp Tyr Lys Asp Val Gly Lys
    50                  55                  60

Phe Val His Lys Val Ser Asp Asn Asp Glu Val Ile Leu Ile Asp Asp
65                  70                  75                  80

Asp Ile Ile Tyr Pro Arg Asp Tyr Val Glu Val Leu Arg Tyr Phe Tyr
                85                  90                  95

Lys Lys Tyr Gln His Leu Asn Ile Ile Val Gly Thr His Gly Ile Ile
            100                 105                 110

Tyr Pro Asp Leu Tyr Asp Gly Ser Val Ser Ser Arg Lys Val Phe Thr
        115                 120                 125

Phe Lys His Ser Leu Lys Arg Pro Arg Val Val Asn Gln Leu Gly Thr
    130                 135                 140

Gly Thr Val Tyr Leu Lys Gly Ser Gln Met Pro Ser Leu Glu Tyr Met
145                 150                 155                 160

Lys Gly Ser Gln Lys Phe Val Asp Val Arg Phe Ser Lys Tyr Met Phe
                165                 170                 175

Glu Lys Gly Ile Gly Leu Ile Cys Ile Pro Arg Gly Ala Asp Trp Gln
            180                 185                 190

Lys Glu Ile Lys Gln Glu Asp Ser Ile Phe Asn Asn Phe Thr Ser Lys
        195                 200                 205

Trp Pro Met Gln Val Ile Gln Glu Val Gln Ile Ile Ala Gly Tyr Ser
    210                 215                 220

Lys Leu Pro Phe Asn Leu Val Lys Glu Ile Glu Phe Asn Lys Asp Ser
225                 230                 235                 240

Leu Leu Met Ser Gln
                245
```

<210> SEQ ID NO 13
<211> LENGTH: 735
<212> TYPE: DNA
<213> ORGANISM: Artificial Sequence
<220> FEATURE:
<223> OTHER INFORMATION: It is synthesized.

<400> SEQUENCE: 13

```
atgataatag ctaatatggc aacatttccc gctagggtag aaatatgtaa acaagtggtt    60
gatagcatct acaaccaggt tgaccaaatt aacctgtgct caacgagtt taagcagatc    120 ccgaaagaat acgcgaagta tcacaaactg aacccggtga ttccggatac cgactataag    180
gatgttggta aatttgtgca caaagttagc gataacgacg aggtgatcct gattgacgat    240
gacatcattt acccgcgtga ctatgtggaa gttctgcgtt acttctataa gaaataccaa    300
```

```
cacctgaaca tcattgttgg tacccacggc atcatttacc cggatctgta tgacggcagc    360
gtgagcagcc gtaaggtttt cacctttaaa cacagcctga agcgtccgcg tgtggttaac    420
cagctgggta ccggcaccgt gtacctgaaa ggtagccaaa tgccgagcct ggagtatatg    480
aagggcagcc agagcttcgt ggatgttcgt tttgcaaaat acatgttcga aaagggtatc    540
ggcctgatct gcattccgcg tggtgcggat tggcaaaagg agatcaaaca ggaagacagc    600
attttcaaca actttaccag caaatggccg atgcaggtga tccaagaagt tcagatcatt    660
gcgggctata gcaagctgcc gtttaacctg gttaaagaga ttgaattcaa caaggacagc    720
ctgctgatga gccaa                                                     735
```

<210> SEQ ID NO 14
<211> LENGTH: 245
<212> TYPE: PRT
<213> ORGANISM: Artificial Sequence
<220> FEATURE:
<223> OTHER INFORMATION: It is synthesized.

<400> SEQUENCE: 14

```
Met Ile Ile Ala Asn Met Ala Thr Phe Pro Ala Arg Val Glu Ile Cys
1               5                   10                  15

Lys Gln Val Val Asp Ser Ile Tyr Asn Gln Val Asp Gln Ile Asn Leu
                20                  25                  30

Cys Phe Asn Glu Phe Lys Gln Ile Pro Lys Glu Tyr Ala Lys Tyr His
            35                  40                  45

Lys Leu Asn Pro Val Ile Pro Asp Thr Asp Tyr Lys Asp Val Gly Lys
        50                  55                  60

Phe Val His Lys Val Ser Asp Asn Asp Glu Val Ile Leu Ile Asp Asp
65                  70                  75                  80

Asp Ile Ile Tyr Pro Arg Asp Tyr Val Glu Val Leu Arg Tyr Phe Tyr
                85                  90                  95

Lys Lys Tyr Gln His Leu Asn Ile Ile Val Gly Thr His Gly Ile Ile
                100                 105                 110

Tyr Pro Asp Leu Tyr Asp Gly Ser Val Ser Ser Arg Lys Val Phe Thr
            115                 120                 125

Phe Lys His Ser Leu Lys Arg Pro Arg Val Val Asn Gln Leu Gly Thr
        130                 135                 140

Gly Thr Val Tyr Leu Lys Gly Ser Gln Met Pro Ser Leu Glu Tyr Met
145                 150                 155                 160

Lys Gly Ser Gln Ser Phe Val Asp Val Arg Phe Ala Lys Tyr Met Phe
                165                 170                 175

Glu Lys Gly Ile Gly Leu Ile Cys Ile Pro Arg Gly Ala Asp Trp Gln
            180                 185                 190

Lys Glu Ile Lys Gln Glu Asp Ser Ile Phe Asn Asn Phe Thr Ser Lys
        195                 200                 205

Trp Pro Met Gln Val Ile Gln Glu Val Gln Ile Ile Ala Gly Tyr Ser
    210                 215                 220

Lys Leu Pro Phe Asn Leu Val Lys Glu Ile Glu Phe Asn Lys Asp Ser
225                 230                 235                 240

Leu Leu Met Ser Gln
                245
```

HEPARIN SKELETON SYNTHASE AND ITS MUTANTS AND APPLICATION

CROSS REFERENCES

This application claims priority to Chinese Patent Application Ser. No. CN202110192424.2 filed on 20 Feb. 2021.

FIELD OF THE INVENTION

The present invention relates to a heparin skeleton synthase and its mutants and application and particularly relates to a heparin skeleton synthase originating from the *Neisseria animaloris*, as well as its six mutants and its application in heparin skeleton synthesis. It pertains to the field of biotechnology.

BACKGROUND OF THE INVENTION

Heparin (HP) is an important glycosaminoglycan composed of repeating disaccharide units formed by D-β-glucuronic acid (or L-α-iduronic acid) and N-acetylglucosamine. It has a great medicinal value. In addition to the anticoagulation-related applications, it can also be used to treat angina pectoris, nephrotic syndrome, severe burns, rheumatoid arthritis, and so on. It has been ranked among the most needed biotechnology drugs across the world all the time.

The heparin is mainly extracted from animal tissues and organs such as bovine lung and porcine intestinal mucosa. However, besides low safety, low yield, large solvent consumption, and severe environmental pollution, the natural extraction method introduces impurity contamination (such as chondroitin sulfate) easily during production. Its product quality is difficult to control because of the raw material differences. The basic units of natural heparin vary in number and structure, and extraction methods will also lead to different chemical modifications, resulting in the differences in the structure, configuration, and molecular weight of the resulting heparin products and ultimately leading to the uneven activity of the final products. As perfect quality monitoring is not feasible in the process, the quality and the safety of the resulting heparin products are not guaranteed.

The widespread contamination of heparin in 2008, which resulted in the deaths of nearly 100 patients, significantly pushed the production of heparin from non-animal sources. Featuring strong stereoselectivity, high yield, mild reaction conditions, and uniform product quality, as well as easiness in the derivation and modification of functional groups, the chemoenzymatic synthesis method is of great significance to the development of new drugs and is expected to grow into an ideal new technique for the synthesis of heparin oligosaccharides. However, what tool enzymes to use in the chemoenzymatic synthesis is a bottleneck that restricts the further development of this strategy.

Two heparin skeleton synthases (N-Acetyl-D-glucosaminyltransferase) of microbial origins with N-acetylglucosamine transferase activity have been reported so far, respectively the KfiA from *Escherichia coli* K5 and the GaKfiA from Epicauta cazieri. The limited number of heparin skeleton synthases restricts not only the theoretical study of the enzymatic properties of the enzyme family but also the scale application of the chemoenzymatic synthesis system of heparin.

*Neisseria animaloris* is a rare zoonotic pathogen generally relating to dog or cat bites. It is mainly found in the mouths of dogs and feline animals and can cause systemic infection in humans and animals after being bitten. Upon search in the database, no glycosaminoglycan skeleton synthase gene from this strain was reported.

SUMMARY OF THE INVENTION

To address the drawbacks in the prior art, the present invention provides a heparin skeleton synthase and its mutants and application. The said heparin skeleton synthase in the invention is the high expression heparin skeleton synthase NaGlcNAc-T derived from *Neisseria animaloris*. The said mutants are six high-activity mutants obtained through site-directed mutagenesis. The said heparin skeleton synthase and its six high-activity mutants can be applied in the synthesis of heparin oligosaccharides.

Definition of Terms

GlcA-pNP: its full name is 4-Nitrophenyl-β-D-glucuronic acid, and it functions as an initial substrate for the synthesis of heparin oligosaccharides;

UDP-GlcNAc: its full name is Uridine diphosphate N-acetylglucosamine, and it functions as an acetylglucosamine donor in the synthesis of heparin oligosaccharides;

UDP-GlcNTFA: its full name is Uridine diphosphate N-trifluoro acetylglucosamine, it determines the substrate specificity of the heparin skeleton synthase and functions as a trifluoro acetylglucosamine donor;

UDP-GalNAz: its full name is Uridine diphosphate-N-azidoacetylgalactosamine, and it determines the substrate specificity of the heparin skeleton synthase and functions as an azidoacetylgalactosamine donor;

UDP-GalNAc: its full name is Uridine diphosphate-N-acetylgalactosamine, and it determines the substrate specificity of the heparin skeleton synthase and functions as an acetylgalactosamine donor;

UDP-Glc: its full name is Uridine diphosphate-N-glucose, and it determines the substrate specificity of the heparin skeleton synthase and functions as a glucose donor;

UDP-Gal: its full name is Uridine diphosphate-N-galactose, and it determines the substrate specificity of the heparin skeleton synthase and functions as a galactose donor.

A technical solution of the present invention is provided below:

A heparin skeleton synthase NaGlcNAc-T with an amino acid sequence as shown in SEQ ID NO.2 and a nucleotide sequence of the coding gene as shown in SEQ ID NO.1.

The said heparin skeleton synthase NaGlcNAc-T in the present invention originates from *Neisseria animaloris*, and its recombinant expression level is 6.8 times that of the existing heparin skeleton synthase KfiA from *Escherichia coli* K5. Upon site-directed mutagenesis of the said heparin skeleton synthase NaGlcNAc-T, the resulting heparin skeleton synthase mutants have higher expression levels.

A heparin skeleton synthase mutant NaGlcNAc-T (C16L) with an amino acid sequence as shown in SEQ ID NO.4 and a nucleotide sequence of the coding gene as shown in SEQ ID NO.3, which is obtained by mutating the cysteine at the site No. 16 in the amino acid sequence of the said heparin skeleton synthase to leucine through site-directed mutagenesis.

A heparin skeleton synthase mutant NaGlcNAc-T (N25P) with an amino acid sequence as shown in SEQ ID NO.6 and a nucleotide sequence of the coding gene as shown in SEQ ID NO.5, which is obtained by mutating the asparagine at the site No. 25 in the amino acid sequence of the said heparin skeleton synthase to proline through site-directed mutagenesis.

A heparin skeleton synthase mutant NaGlcNAc-T (I30L) with an amino acid sequence as shown in SEQ ID NO.8 and a nucleotide sequence of the coding gene as shown in SEQ ID NO.7, which is obtained by mutating the isoleucine at the site No. 30 in the amino acid sequence of the said heparin skeleton synthase to leucine through site-directed mutagenesis.

A heparin skeleton synthase mutant NaGlcNAc-T (I111S) with an amino acid sequence as shown in SEQ ID NO.10 and a nucleotide sequence of the coding gene as shown in SEQ ID NO.9, which is obtained by mutating the isoleucine at the site No. 111 in the amino acid sequence of the said heparin skeleton synthase to serine through site-directed mutagenesis.

A heparin skeleton synthase mutant NaGlcNAc-T (S165K) with an amino acid sequence as shown in SEQ ID NO.12 and a nucleotide sequence of the coding gene as shown in SEQ ID NO.11, which is obtained by mutating the serine at the site No. 165 in the amino acid sequence of the said heparin skeleton synthase to lysine through site-directed mutagenesis.

A heparin skeleton synthase mutant NaGlcNAc-T (S172A) with an amino acid sequence as shown in SEQ ID NO.14 and a nucleotide sequence of the coding gene as shown in SEQ ID NO.13, which is obtained by mutating the serine at the site No. 172 in the amino acid sequence of the said heparin skeleton synthase to alanine through site-directed mutagenesis.

The said heparin skeleton synthase mutants in the present invention also have high recombinant expression levels, and their enzymatic activity remains equable or improves to different extents compared to the heparin skeleton synthase NaGlcNAc-T.

A recombinant vector, which is obtained by inserting the coding genes of the said heparin skeleton synthase NaGlcNAc-T or the said heparin skeleton synthase mutants into a plasmid vector.

Preferably according to the present invention, the said plasmid vector is pET30a(+).

In the present invention, the recombinant vector containing the target gene is synthesized by Nanjing Genscript Company.

A recombinant strain, which is obtained by transforming the said recombinant vector into a host cell.

Preferably according to the present invention, the said host cell is *Escherichia coli*; more preferably, it is *Escherichia coli* BL21 (DE3) that contains pGro7 plasmids.

The said heparin skeleton synthase NaGlcNAc-T or the said heparin skeleton synthase mutants are applied in the synthesis of the heparin disaccharide chains.

Preferably according to the present invention, the said application is to produce the heparin skeleton disaccharides with the structure of GlcNAc-GlcA-pNP with GlcA-pNP as the initial receptor and UDP-GlcNAc as the donor.

Beneficial Effects

The heparin skeleton synthase NaGlcNAc-T disclosed in the present invention is a heparin skeleton synthase of a new origin and with GlcNAc transferase activity. It uses GlcA-pNP and UDP-GlcNAc as substrates to synthesize the heparin disaccharide skeleton effectively under optimal conditions. Upon preliminary expression analysis, the NaGlcNAc-T can express more than 100 mg soluble active protein based on per liter of ordinary LB medium, and compared to the heparin skeleton synthase KfiA from *Escherichia coli* K5 that has been put into use, its expressed enzyme activity per liter of fermentation liquor is improved by 5.22 times. Additionally, the present invention also obtains several NaGlcNAc-T mutants, which have higher activity than KfiA, through site-directed mutagenesis. The invention improves the GlcNAc transfer and synthesis efficiency during heparin skeleton synthesis, greatly promotes the application development of heparin biomimetic synthesis, and opens a new page for the research and development of glycosaminoglycan.

Figure 2:
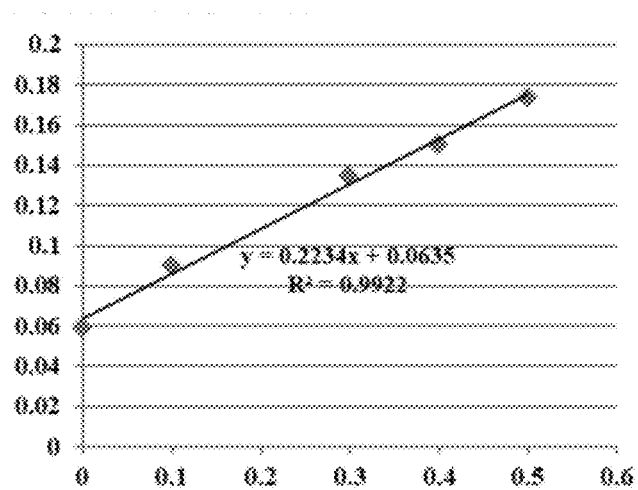
Figure 3:
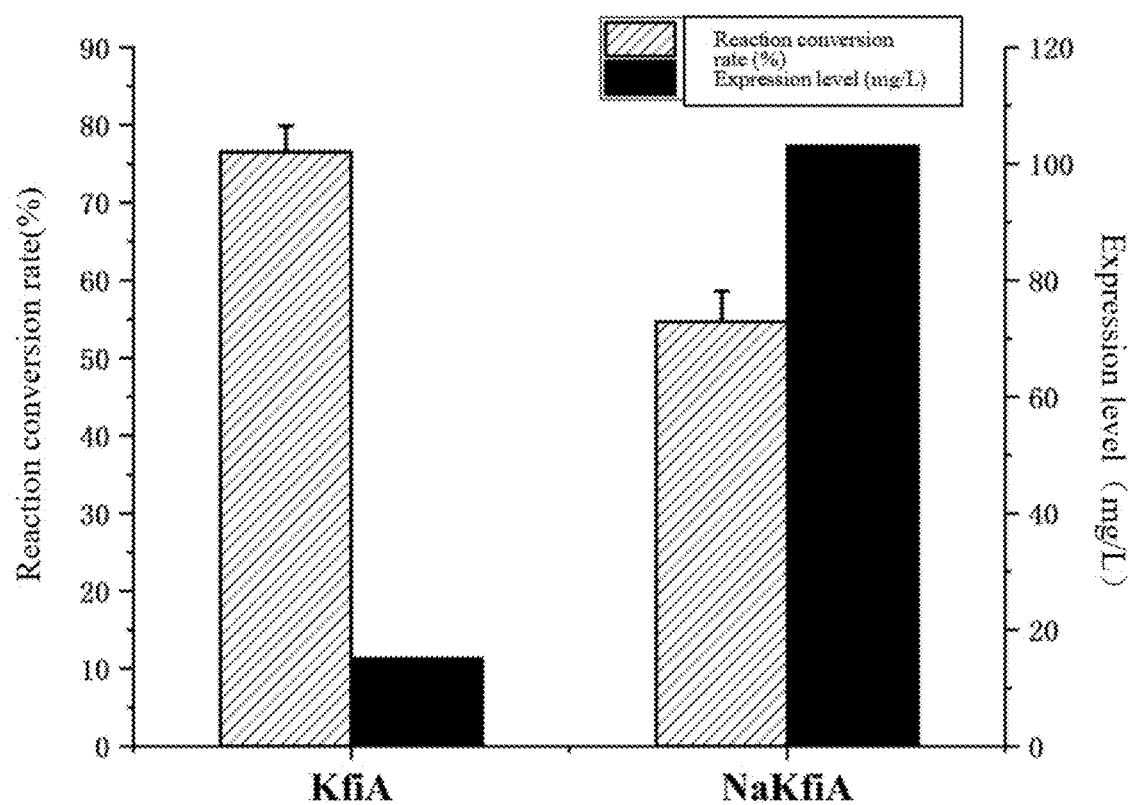
Figure 4:
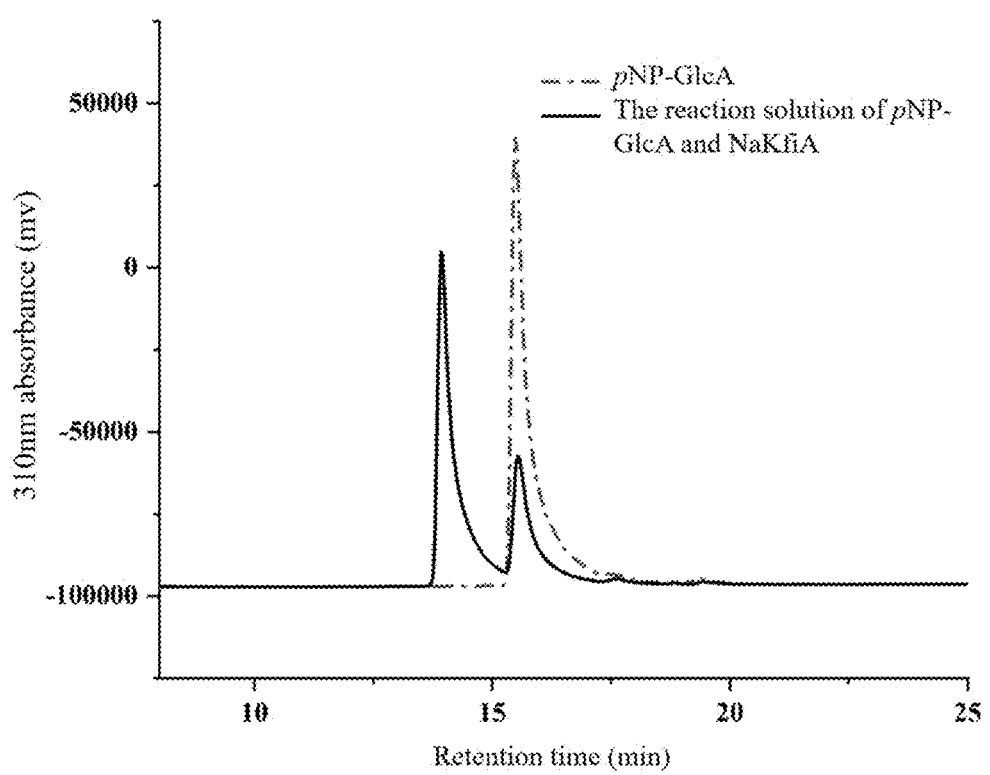
Figure 5:
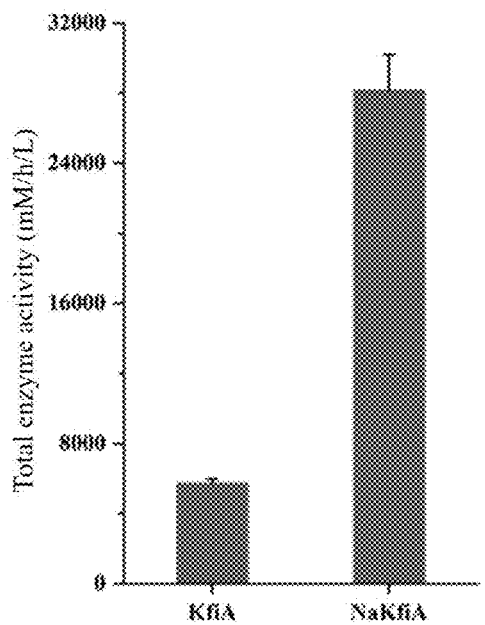
Figure 6:
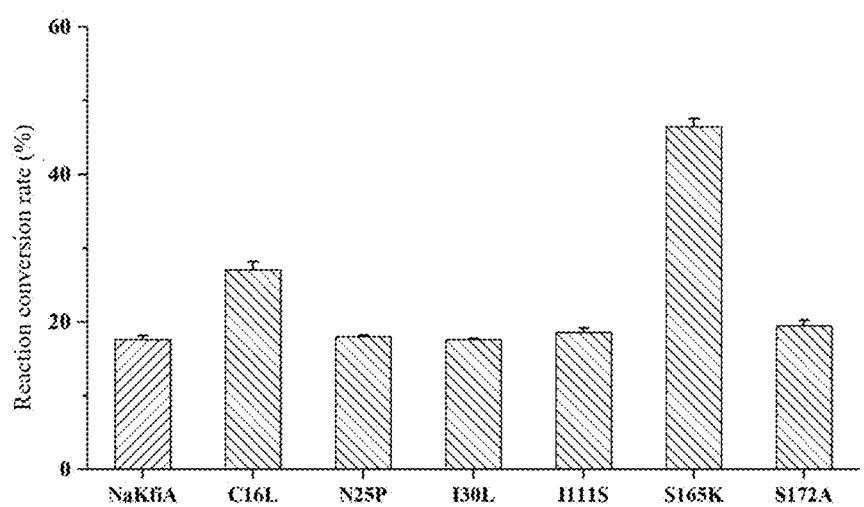
Figure 7:
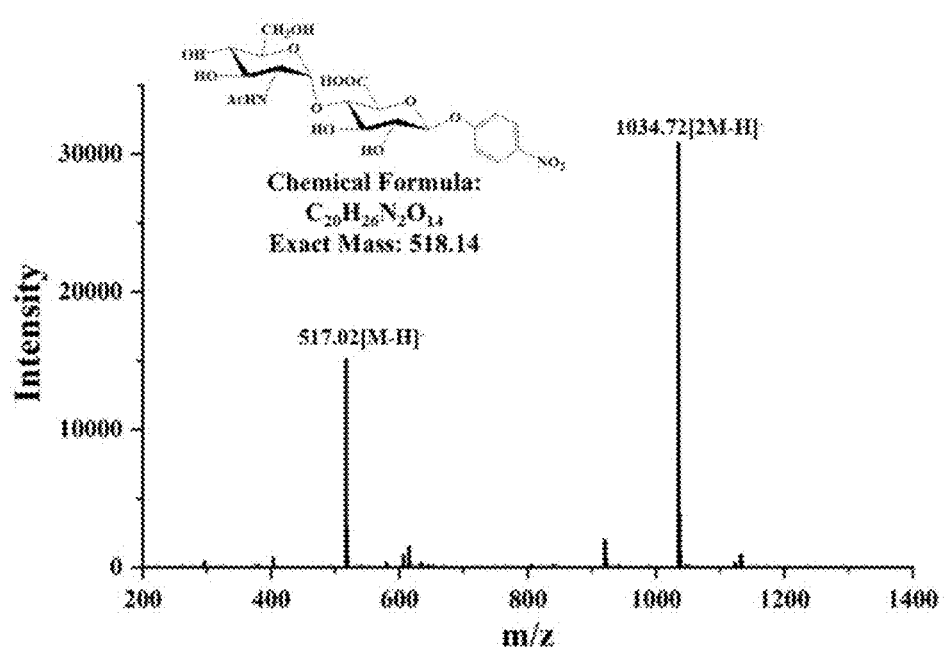
Figure 8:
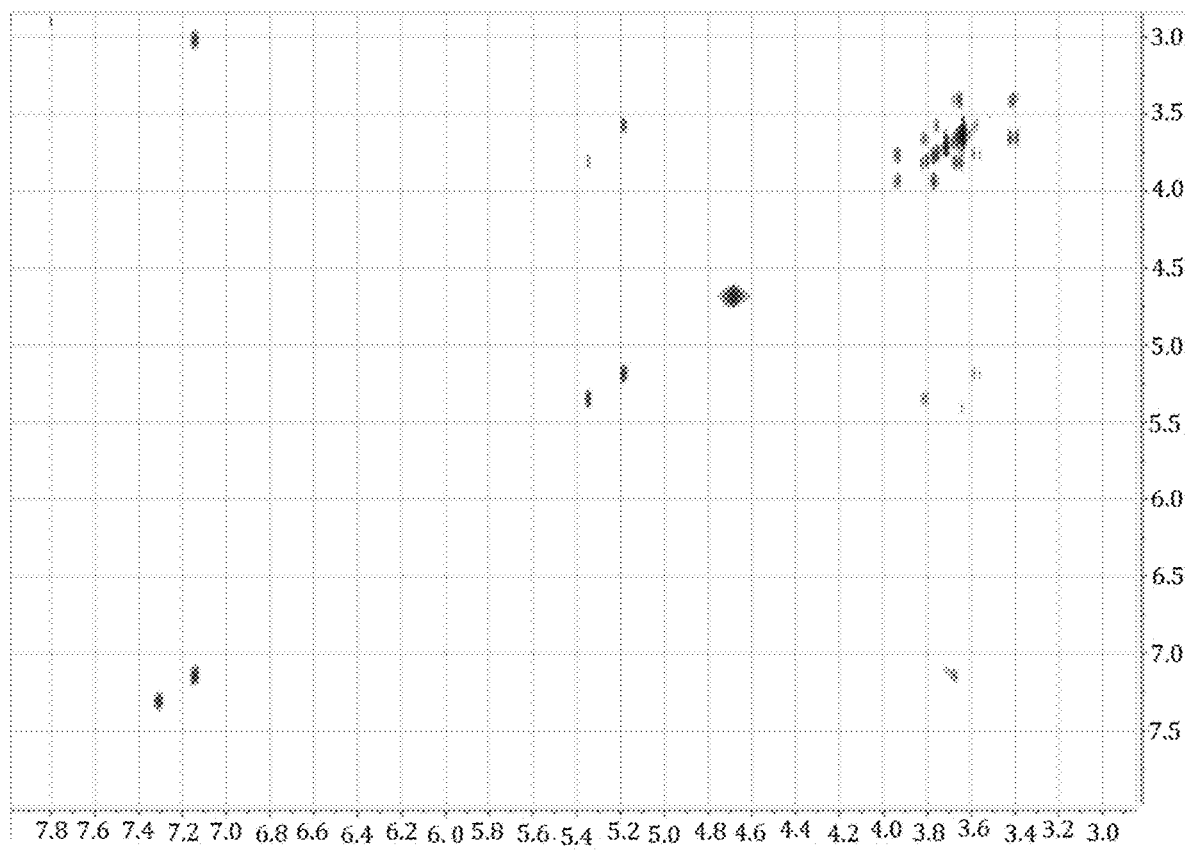
Figure 9:
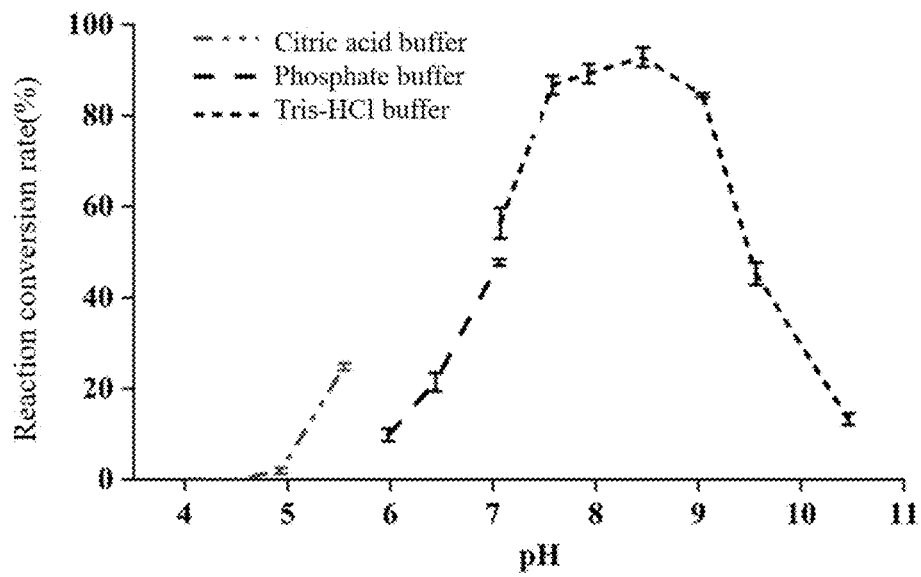

Where: M is the marker; the rest of the strips are the purified recombinant proteins expressed by the NaGlcNAc-T and its mutants, with NaKfiA corresponding to NaGlcNAc-T, C16L corresponding to NaGlcNAc-T (C16L), N25P corresponding to NaGlcNAc-T (N25P), I30L corresponding to NaGlcNAc-T (I30L), I111S corresponding to NaGlcNAc-T (I111S), S165K corresponding to NaGlcNAc-T (S165K), and S172A corresponding to NaGlcNAc-T (S172A);

FIG. 2 is the protein quantitative standard curve of the heparin skeleton synthase NaGlcNAc-T;

FIG. 3 is the bar graph of the expression levels and receptor substrate reaction conversion rates of the heparin skeleton synthase NaGlcNAc-T and the heparin skeleton synthase KfiA;

FIG. 4 is the HPLC chromatogram of the reaction products of the heparin skeleton synthase NaGlcNAc-T;

FIG. 5 is the bar graph of the total enzyme activity of the heparin skeleton synthase NaGlcNAc-T and the heparin skeleton synthase KfiA;

FIG. 6 is the bar graph of the receptor substrate reaction conversion rates of the heparin skeleton synthase NaGlcNAc-T and its mutants;

FIG. 7 is the mass spectrogram of the reaction product GlcNAc-GlcA-pNP of the heparin skeleton synthase NaGlcNAc-T;

FIG. 8 is the $^1$H-H COSY of the reaction product GlcNAc-GlcA-pNP of the heparin skeleton synthase NaGlcNAc-T;

FIG. 9 shows the reaction conversion rate curve of the receptor substrate when the heparin skeleton synthase NaGlcNAc-T is catalyzing oligosaccharide synthesis at different pH values in vitro.

Figure 10:
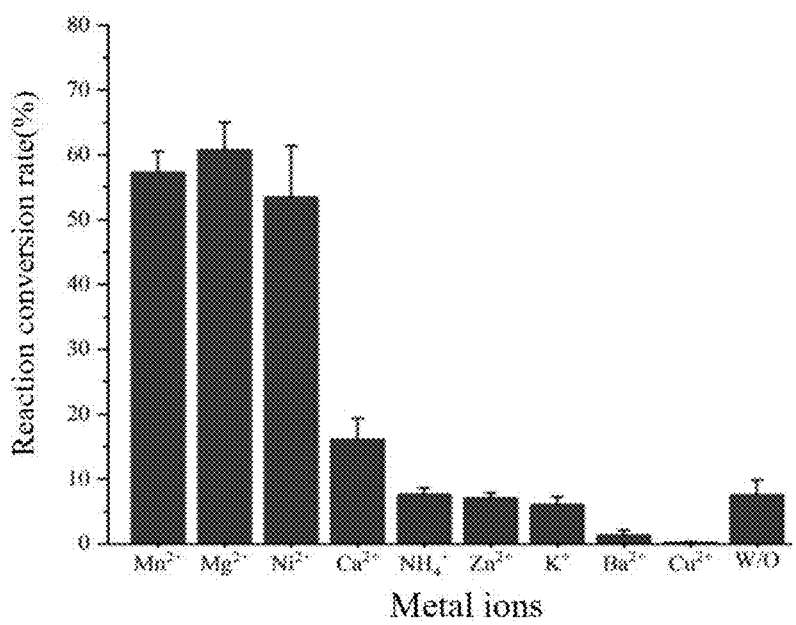

FIG. 10 shows the reaction conversion rate bar graph of the receptor substrate when the heparin skeleton synthase NaGlcNAc-T is catalyzing oligosaccharide synthesis under the action of different metal ions in vitro.

Figure 11:
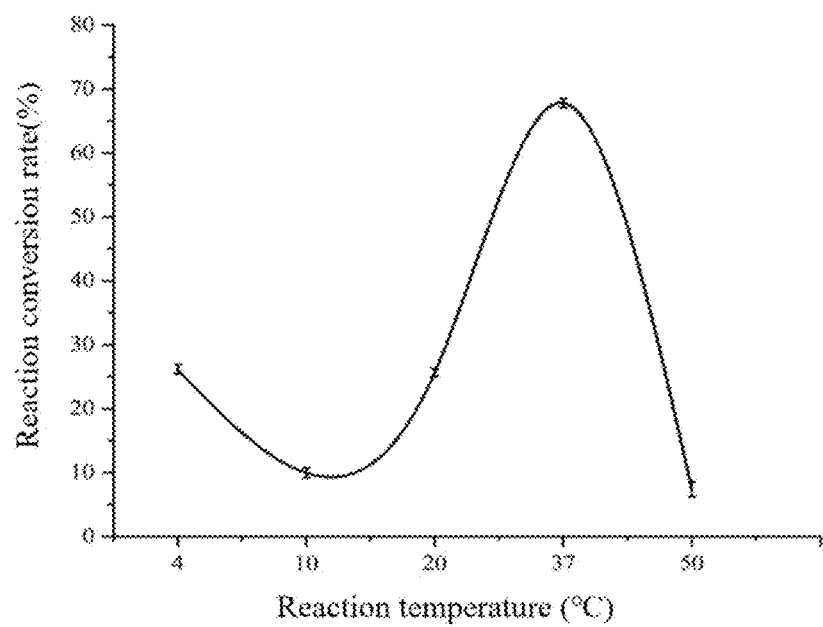

FIG. 11 shows the reaction conversion rate curve of the receptor substrate when the heparin skeleton synthase NaGlcNAc-T is catalyzing oligosaccharide synthesis at different temperatures in vitro.

Figure 12:
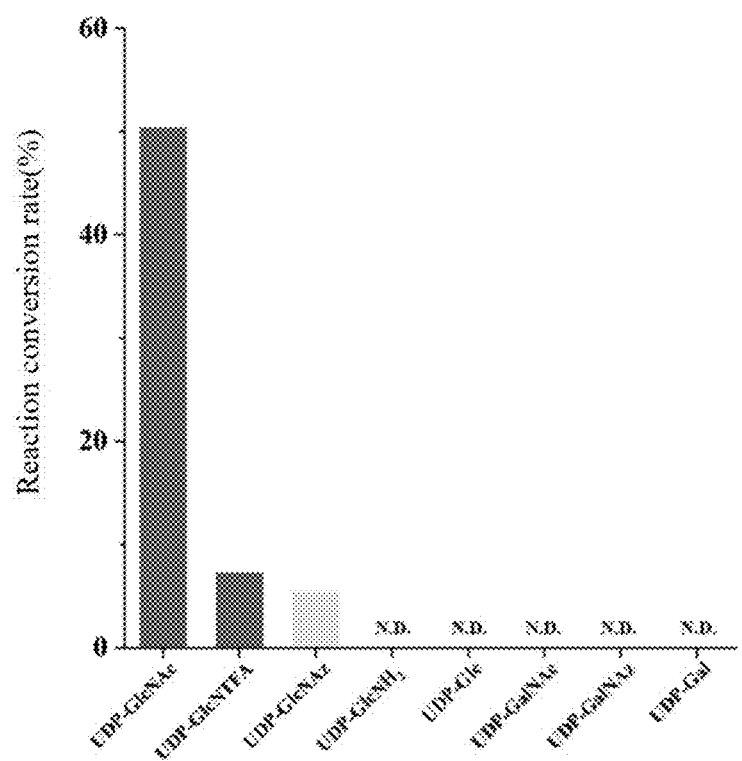

FIG. 12 shows the reaction conversion rate bar graph of the receptor substrate when the heparin skeleton synthase NaGlcNAc-T is catalyzing oligosaccharide synthesis based on different donor substrates in vitro.

Where: N.D. denotes that the substrate cannot be catalyzed by the NaGlcNAc-T.

EMBODIMENTS

The technical solution disclosed in the present invention is further described as follows with reference to the embodiments and drawings. However, the present invention is not limited thereto. Unless otherwise specified, the technical means used in the invention are all known to those skilled in the field.

Upon search in the bioinformatics database through Blast sequence alignment, the author of the invention has found that the amino acid sequence formed by a gene of the *Neisseria animaloris* (ATCC29858) is 55.7% homologous to that of the previously reported heparin skeleton synthase KfiA from *Escherichia coli* K5. Therefore, it is speculated that the protein product expressed by this gene may have heparin skeleton synthase activity. Upon protein expression in the *Escherichia coli* expression system, the gene is named NaGlcNAc-T, with a nucleotide sequence as shown in SEQ ID NO.1, and the protein product expressed by it is named NaGlcNAc-T, with an amino acid sequence as shown in SEQ ID NO.2.

Additionally, the author of the invention has conducted sequence homology analysis for the searched KfiA homologous sequence by performing multiple sequence alignment with EMBL Clustal Omega and analyzing the highly conserved region of the amino acid sequence with the Jalview software. Also, the author has performed protein simulation modeling for NaGlcNAc-T with Swiss-Model and predicted the active center of the enzyme with HotSpot Wizard 2.0. The findings show that sites No. 16, No. 25, No. 30, No. 111, No. 165, and No. 172 in the amino acid sequence of NaGlcNAc-T are located near the active center and the highly conserved region, and site-directed mutagenesis of these sites is very likely to improve the catalytic activity of the NaGlcNAc-T. Hence, with reference to the dominant amino acids at these six sites according to the homology analysis, the invention has designed six mutants, respectively NaGlcNAc-T (C16L), NaGlcNAc-T (N25P), NaGlcNAc-T (I30L), NaGlcNAc-T (I111S), NaGlcNAc-T (S165K), and NaGlcNAc-T (S172A). Among them, the mutant NaGlcNAc-T (C16L) is with a nucleotide sequence as shown in SEQ ID NO.3 and an amino acid sequence as shown in SEQ ID NO.4; the mutant NaGlcNAc-T (N25P) is with a nucleotide sequence as shown in SEQ ID NO.5 and an amino acid sequence as shown in SEQ ID NO.6; the mutant NaGlcNAc-T (I30L) is with a nucleotide sequence as shown in SEQ ID NO.7 and an amino acid sequence as shown in SEQ ID NO.8; the mutant NaGlcNAc-T (I111S) is with a nucleotide sequence as shown in SEQ ID NO.9 and an amino acid sequence as shown in SEQ ID NO.10; the mutant NaGlcNAc-T (S165K) is with a nucleotide sequence as shown in SEQ ID NO.11 and an amino acid sequence as shown in SEQ ID NO.12; the mutant NaGlcNAc-T (S172A) is with a nucleotide sequence as shown in SEQ ID NO.13 and an amino acid sequence as shown in SEQ ID NO.14.

The substrate saccharide reagents used in the present invention are all purchased from the Sigma Company. All the plasmids of NaGlcNAc-T and its mutants are synthesized by Nanjing Genscript Company. The BL21 (DE3) competent cells containing pGro7 molecular chaperones are purchased from Takara. The HPLC testing method used is YMC's amino column method, the liquid phase system is from Shimadzu JAPAN, and the UV testing system is SPD-20A. The ultraviolet absorption of the components from the catalysate of the NaGlcNAc-T and its mutants upon separation by chromatographic column is tested at 310 nm and 254 nm respectively under the HPLC mobile phase conditions as shown in Table 1:

TABLE 1

| The HPLC analysis method used to test the heparin oligosaccharide | | |
|---|---|---|
| Time/min | 1M dipotassium phosphate | Ultrapure water |
| 0 | 0% | 100% |
| 30 | 60% | 40% |
| 31 | 100% | 0% |
| 33 | 100% | 0% |
| 43 | 0% | 100% |

Embodiment 1. Recombinant Protein Expression and Purification of the Heparin Skeleton Synthase NaGlcNAc-T and its Mutants Construction of Expressing Strains The recombinant plasmids pET30a(+)-NaGlcNAc-T synthesized by Nanjing Genscript Company are transformed into the *Escherichia coli* BL21 (DE3) competent cells containing pGro7 molecular chaperones and then cultured on LB plates containing kanamycin (100 μg/mL) and chloramphenicol (37 μg/mL) for 12 h. After that, transformants are screened (negative control experiments are carried out at the same time) to obtain the positive ones.

Following the above method, positive transformants are obtained for the six mutants, NaGlcNAc-T (C16L), NaGlcNAc-T (N25P), NaGlcNAc-T (I30L), NaGlcNAc-T (I111S), NaGlcNAc-T (S165K), and NaGlcNAc-T (S172A) respectively.

(2) Recombinant Protein Expression and Purification of the NaGlcNAc-T and its Mutants Single colonies of the NaGlcNAc-T positive transformants are picked and inoculated on a 30 mL sterile LB culture medium (containing 100 μg/mL kanamycin and 37 μg/mL chloramphenicol) for activated culture (37° C., 225 r/min); after activated culture overnight, the bacteria solution is then transferred into 1 L LB medium (containing 100 μg/mL kanamycin and 37 μg/mL chloramphenicol) at an inoculum size of 1% for propagation; the medium is shaken under the conditions of 37° C. and 225 r/min for about 4 hours until the $OD_{600}$ reaches about 0.8; then, IPTG with a final concentration of 0.5 mM and 1 mg/mL L-arabinose are added for induced expression under the conditions of 22° C. and 225 r/min for 16-18 hours; then, bacterial cells are collected, re-suspended with equilibration buffer (20 mM Tris-HCl, pH=8.00; 0.5M NaCl; 10 mM imidazole), and crushed by ultrasonic wave on ice (operating for 3 s and pausing for 5 s alternately; amplitude: 33%; energy: 1500KJ; 4° C.) for 30 minutes; the crushed bacterial cells are then centrifuged at 12000 rpm for 20 min (4° C.); the resulting supernatant is filtered by 0.22 μm filter membrane and purified by nickel column; after loading, the samples are rinsed by the equilibration buffer and then the impurity washing buffer (20 mM Tris-HCl, pH=8.00; 0.5M NaCl; 40 mM imidazole) to remove the undesired miscellaneous proteins and finally eluted by the elution buffer (20 mM Tris-HCl, pH=8.00; 0.5M NaCl; 250 mM imidazole) to obtain the target protein. The purified protein is stored in 20% glycerin and sub-packed in tubes before being put into a −80° C. freezer.

Following the above method, purified recombinant proteins are obtained for the six mutants, NaGlcNAc-T (C16L), NaGlcNAc-T (N25P), NaGlcNAc-T (I30L), NaGlcNAc-T (I111S), NaGlcNAc-T (S165K), and NaGlcNAc-T (S172A) respectively.

Figure 1:
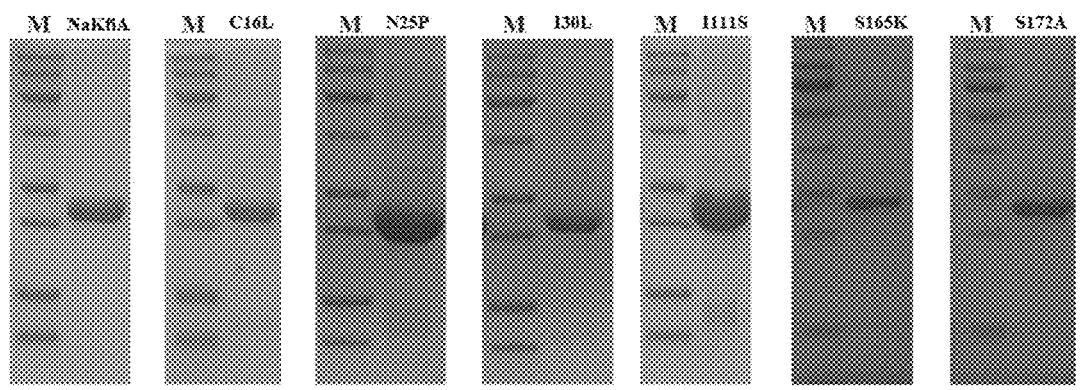
FIG. 1 shows the SDS-PAGE testing results of the soluble expression and purification of the heparin skeleton synthase NaGlcNAc-T and its mutants in recombinant *Escherichia coli*.

The purified recombinant proteins of the NaGlcNAc-T and its mutants are identified by sodium dodecyl sulfate polyacrylamide gel electrophoresis (SDS-PAGE), as shown in FIG. 1. The results show that the NaGlcNAc-T and its mutants (NaGlcNAc-T (C16L), NaGlcNAc-T (N25P), NaGlcNAc-T (I30L), NaGlcNAc-T (I111S), NaGlcNAc-T (S165K), and NaGlcNAc-T (S172A)) are all successfully purified following the above method, with a relative purity of above 90%.

A BCA protein assay kit (Beyotime P0011) is used to quantify the NaGlcNAc-T: first, an appropriate amount of BCA working solution is prepared by mixing 50 parts of BCA reagent A and 1 part of BCA reagent B (50:1 by volume) evenly; then, the standard substance is added in the standard wells of a 96-well plate at the volume of 0, 4, 8, 12, 16, and 20 µL respectively and supplemented by standard dilution buffer to 20 µL each to prepare 0, 0.1, 0.2, 0.3, 0.4, and 0.5 mg/mL standard substance solutions; then 20 µL samples are added in each sample well of the 96-well plate, and 200 µL BCA working solution is added in each well; after keeping them still for 20-30 minutes under 37° C., the A562 values are measured with ELIASA, based on which a standard curve is plotted; finally, the protein concentration of the samples is calculated according to the standard curve and the sample volume used.

The protein quantitative standard curve of the heparin skeleton synthase NaGlcNAc-T is shown in FIG. 2. According to the determination, the recombinant expression of NaGlcNAc-T is as high as 102 mg/L per liter of LB medium, which is 6.8 times that (about 15 mg/L) of the heparin skeleton synthase KfiA from *Escherichia coli* K5 (the two follow the same way of expression), as shown in FIG. 3. Therefore, the NaGlcNAc-T has a higher expression level and a great prospect of industrial application.

Upon expression level determination of the six mutants (NaGlcNAc-T (C16L), NaGlcNAc-T (N25P), NaGlcNAc-T (I30L), NaGlcNAc-T (I111S), NaGlcNAc-T (S165K), and NaGlcNAc-T (S172A) respectively following the above method, it is found that the six mutants also have higher expression levels than the heparin skeleton synthase KfiA from *Escherichia coli* K5.

Embodiment 2. Activity Verification of the Heparin Skeleton Synthase NaGlcNAc-T and its Mutants GlcNAc Transferase Activity Verification of the Heparin Skeleton Synthase NaGlcNAc-T A reaction system with the commercially available GlcA-pNP (final concentration: 0.2 mM) as the receptor substrate and the UDP-GlcNAc (final concentration: 0.3 mM) as the donor substrate is constructed as shown in Table 2; the reaction system is placed in a 37° C. water bath kettle to react for 4 hours and then heated by boiling water for 5 min to stop the reaction by inactivating the enzyme; then, the reaction solution is filtered by 0.22 µm filter membrane and detected by HPLC according to the method described in Table 1. The pNP group of the monosaccharide receptor shows specific absorption at the 310 nm UV test wavelength, and the flow rate of the mobile phase is 0.5 mL/min.

Following the same method, the GlcNAc transferase activity can be tested for the six mutants, NaGlcNAc-T (C16L), NaGlcNAc-T (N25P), NaGlcNAc-T (I30L), NaGlcNAc-T (I111S), NaGlcNAc-T (S165K), and NaGlcNAc-T (S172A) respectively.

TABLE 2

The reaction system for the GlcNAc transferase activity verification of NaGlcNAc-T and its mutants

| GlcA-pNP | UDP-GalNAc | $Mn^{2+}$ | Tris-HCl(pH 7.0) | Protein | Total |
|---|---|---|---|---|---|
| 0.2 mM | 0.3 mM | 20 mM | 50 mM | 20 µg | 400 µL |

According to the testing results in FIG. 4, the NaGlcNAc-T and its mutants all have GlcNAc transferase activity and can transfer the GlcNAc group to the non-reducing end of the GlcA-pNP to produce the heparin disaccharide GlcNAc-GlcA-pNP. The reaction conversion rate of the receptor donor is as shown in FIG. 3. Based on the reaction conversion rate and the expression level of the protease, the total activity of protease can be calculated, as shown in FIG. 5. The total enzyme activity of the NaGlcNAc-T per fermentation liquor is 5.22 times that of the heparin skeleton synthase KfiA from *Escherichia coli* K5.

The activity of the six mutants is determined based on the reaction system in Table 2 and the above treatment method. Upon reaction for 1 h in a 37° C. water bath kettle, the reaction conversion rates of the donor substrate GlcA-pNP for the mutants are shown in FIG. 6. As can be seen from the results, the mutants have remained stable or improved to different extents compared to the NaGlcNAc-T in terms of activity, with the mutants NaGlcNAc-T (C16L) and NaGlcNAc-T (S165K) performing best. These mutants can serve as tool enzymes for heparin disaccharide chain synthesis with high efficiency (2) Mass Spectrum Verification of the Heparin Disaccharide GlcNAc-GlcA-pNP To verify whether the above active reaction products are of the GlcNAc-GlcA-pNP structure, an electrospray ionization mass spectrometry (ESI-MS) analysis is conducted. The active reaction is carried out on a large scale to obtain sufficient disaccharide products. Upon purification through P2 column, an MS analysis is conducted for the resulting products on Thermo LCQ-Deca. All samples of MS analysis are prepared by dissolving the products in 50% methanol. The MS experiments are conducted in a negative ion mode, the electrospray voltage is 5 kV, and the capillary temperature is 275° C.

As can be seen from the mass spectrometry analysis results in FIG. 7, the mass spectrometry shows peaks (517.02) with a molecular weight consistent with that of GlcNAc-GlcA-pNP ($M_w$=518.14) after it removes a proton, as well as diploid peaks (1034.72), proving that the resulting product is GlcNAc-GlcA-pNP.

(3) NMR Verification of the Heparin Disaccharide GlcNAc-GlcA-pNP

About 1 mg of the above active reaction product GlcNAc-GlcA-pNP is dissolved in 500 µL heavy water, and $^1$H-NMR is collected by a 600 M NMR spectrometer. The $^1$H-H COSY spectrum is shown in FIG. 8, wherein the signal with a chemical shift value of 5.35 (d, J=4.15 Hz, 1H) indicates that the bond type between GlcNAc and GlcA is α bond, thus confirming that the synthesized disaccharide is a heparin skeleton.

Embodiment 3 Characterization of the Heparin Skeleton Synthase NaGlcNAc-T and its Mutants Determination of the Optimal Reaction pH Values of the Enzymes In Vitro A reaction system as shown in Table 2 is used, and all conditions are maintained unchanged except for the pH value of the buffer solution. The Tris-HCl buffer is changed to citric acid/phosphate/Tris-HCl buffer of different pH values to set up 12 pH gradient points (4.5, 5.0, 5.5, 6.0, 6.5, 7.0, 7.5, 8.0, 8.5, 9.0, 9.5, and 10.5) with each gradient consisting of three parallel groups, while the other conditions are maintained the same.

As can be seen from the results in FIG. 9, the enzymes are active in a wide range of pH (6.5-9.5), with the optimal pH value falling at 8.5.

(2) Determination of the Optimal Metal Ion for the Reaction of the Enzymes In Vitro Except for the metal ion, all conditions of the reaction system are maintained unchanged. The $Mn^{2+}$ is then changed to $Mg^{2+}$, $Mn^{2+}$, $Ni^{2+}$, $NH_4^+$, $Cu^{2+}$, $Ca^{2+}$, $K^+$, $Ba^{2+}$, or $Zn^{2+}$ of the same concentration for reaction. Three parallel experimental groups and a blank group are set up for each kind of metal ion. The other conditions are maintained the same.

As can be seen from the results in FIG. 10, the enzymes all have optimal catalytic activity in the presence of $Mn^{2+}$, $Mg^{2+}$, and $Ni^{2+}$, while their activity will be reduced when the metal ions are absent.

(3) Study on the Influence of Reaction Temperature on Enzyme Activity

A reaction system as shown in Table 2 is used, and five temperature gradient points (4° C., 10° C., 20° C., 37° C., and 50° C.) are set up for enzyme reaction with each gradient consisting of three parallel groups. The influence of the reaction temperature on the enzyme activity is then measured. The other conditions are maintained the same.

As can be seen from the results in FIG. 11, the optimum reaction temperature of the enzymes is around 37° C.

Upon characterization of the six mutants NaGlcNAc-T (C16L), NaGlcNAc-T (N25P), NaGlcNAc-T (I30L), NaGlcNAc-T (I111S), NaGlcNAc-T (S165K), and NaGlcNAc-T (S172A) respectively following the above method, it is found that the six mutants have similar properties as the heparin skeleton synthase NaGlcNAc-T. They also have activity in a wide pH range (6.5-9.5), present the optimal catalytic activity in the presence of $Mn^{2+}$, $Mg^{2+}$, and $Ni^{2+}$ and a reduced activity when the metal ions are absent, and have the optimum reaction temperature at 37° C.

Embodiment 4 Donor Specificity Study of the Heparin Skeleton Synthase NaGlcNAc-T To determine the substrate specificity of the NaGlcNAc-T, a reaction system as shown in Table 2 with the commercially available GlcA-pNP as the receptor and the UDP-GlcNAc or another UDP-glucose of a similar structure (UDP-GalNAc, UDP-Glc, UDP-Gal, UDP-GlcNTFA, UDP-GalNAz, UDP-GlcNAz, and UDP-$GlcNH_2$) is used for reactions. All the reactions are performed in a 37° C. water bath kettle for 4 hours. Finally, the reaction products are analyzed by HPLC according to the method described in Table 1.

As can be seen from the results in FIG. 12, when the receptor is the monosaccharide GlcA-pNP, the heparin skeleton synthase NaGlcNAc-T can also use UDP-GlcNTFA and UDP-GlcNAz as substrates in addition to the natural substrate UDP-GlcNAc in the experimental groups, but the extent of reaction is not that intensive.

Upon donor specificity study of the six mutants NaGlcNAc-T (C16L), NaGlcNAc-T (N25P), NaGlcNAc-T (I30L), NaGlcNAc-T (I111S), NaGlcNAc-T (S165K), and NaGlcNAc-T (S172A) respectively following the above method, it is found that the six mutants have similar donor specificity as the heparin skeleton synthase NaGlcNAc-T. In addition to the natural substrate UDP-GlcNAc, they can also use UDP-GlcNTFA and UDP-GlcNAz as substrates, provided however that the extent of reaction is not that intensive.

---

What is claimed is:

1. A mutant heparin skeleton synthase (NaGlcNAc-T) is obtained from a wild-type NaGlcNAc-T, wherein the mutant NaGlcNAc-T is selected from the group consisting of a mutant heparin skeleton synthase having C16L mutation and comprises the amino acid sequence of SEQ ID NO: 4, a mutant heparin skeleton synthase having N25P mutation and comprises the amino acid sequence of SEQ ID NO: 6, a mutant heparin skeleton synthase having I30L mutation and comprises the amino acid sequence of SEQ ID NO: 8, a mutant heparin skeleton synthase having I111S mutation and comprises the amino acid sequence of SEQ ID NO: 10, a mutant heparin skeleton synthase having S165K mutation and comprises the amino acid sequence of SEQ ID NO: 12, a mutant heparin skeleton synthase having S172A mutation and comprises the amino acid sequence of SEQ ID NO: 14.

2. The mutant heparin skeleton synthase, NaGlcNAc-T, according to claim 1, wherein the mutant NaGlcNAc-T is the mutant heparin skeleton synthase having C16L mutation and comprises the amino acid sequence of SEQ ID NO: 4.

3. The mutant heparin skeleton synthase, NaGlcNAc-T, according to claim 1, wherein the mutant NaGlcNAc-T is the mutant heparin skeleton synthase having mutation N25P and comprises the amino acid sequence of SEQ ID NO: 6.

4. The mutant heparin skeleton synthase, NaGlcNAc-T, according to claim 1, wherein the mutant NaGlcNAc-T is the mutant heparin skeleton synthase having I30L mutation and comprises the amino acid sequence of SEQ ID NO: 8.

5. The mutant heparin skeleton synthase, NaGlcNAc-T, according to claim 1, wherein the mutant NaGlcNAc-T is the mutant heparin skeleton synthase having I111S mutation and comprises the amino acid sequence of SEQ ID NO: 10.

6. The mutant heparin skeleton synthase, NaGlcNAc-T, according to claim 1, wherein the mutant NaGlcNAc-T is the mutant heparin skeleton synthase having S165K mutation and comprises the amino acid sequence of SEQ ID NO: 12.

7. The mutant heparin skeleton synthase, NaGlcNAc-T, according to claim 1, wherein the mutant NaGlcNAc-T is the mutant heparin skeleton synthase having S172A mutation and comprises the amino acid sequence of SEQ ID NO: 14.

* * * * *